United States Patent
Hong et al.

(10) Patent No.: US 11,793,799 B2
(45) Date of Patent: Oct. 24, 2023

(54) SUSTAINED-RELEASE ANESTHETIC COMPOSITIONS AND METHODS OF PREPARATION THEREOF

(71) Applicants: TLC Biopharmaceuticals, Inc., South San Francisco, CA (US); Taiwan Liposome Co., Ltd., Taipei (TW)

(72) Inventors: Keelung Hong, San Francisco, CA (US); Hao-Wen Kao, Taipei (TW); Yi-Yu Lin, Taipei (TW); Luke S. S. Guo, San Francisco, CA (US)

(73) Assignees: TLC Biopharmaceuticals Inc., South San Francisco, CA (US); Taiwan Liposome Co., Ltd., Taipei (TW)

(*) Notice: Subject to any disclaimer, the term of this patent is extended or adjusted under 35 U.S.C. 154(b) by 479 days.

(21) Appl. No.: 16/642,762

(22) PCT Filed: Aug. 28, 2018

(86) PCT No.: PCT/US2018/048329
§ 371 (c)(1),
(2) Date: Feb. 27, 2020

(87) PCT Pub. No.: WO2019/046293
PCT Pub. Date: Mar. 7, 2019

(65) Prior Publication Data
US 2020/0188374 A1 Jun. 18, 2020

Related U.S. Application Data

(60) Provisional application No. 62/621,730, filed on Jan. 25, 2018, provisional application No. 62/550,983, filed on Aug. 28, 2017.

(51) Int. Cl.
| | | |
|---|---|---|
| *A61K 31/445* | (2006.01) | |
| *A61P 23/00* | (2006.01) | |
| *A61K 9/06* | (2006.01) | |
| *A61K 47/22* | (2006.01) | |
| *A61K 47/24* | (2006.01) | |
| *A61K 47/28* | (2006.01) | |

(52) U.S. Cl.
CPC ........... *A61K 31/445* (2013.01); *A61K 9/06* (2013.01); *A61K 47/22* (2013.01); *A61K 47/24* (2013.01); *A61K 47/28* (2013.01); *A61P 23/00* (2018.01)

(58) Field of Classification Search
CPC .................................................. A61K 31/445
See application file for complete search history.

(56) References Cited

U.S. PATENT DOCUMENTS

| | | | |
|---|---|---|---|
| 5,244,678 A | 9/1993 | Legros et al. | |
| 6,149,937 A | 11/2000 | Legros et al. | |
| 6,926,905 B2 | 8/2005 | Grant et al. | |
| 7,357,944 B2 | 4/2008 | Bolotin et al. | |
| 8,182,835 B2 | 5/2012 | Kim et al. | |
| 2015/0250724 A1* | 9/2015 | Yamashita | A61K 9/0019 604/272 |
| 2015/0257024 A1 | 9/2015 | Baid et al. | |
| 2015/0359891 A1* | 12/2015 | Chen | A61K 9/0019 514/447 |
| 2017/0035777 A1 | 2/2017 | Ottoboni et al. | |

FOREIGN PATENT DOCUMENTS

| | | | |
|---|---|---|---|
| WO | 97/34582 A1 | 9/1997 | |
| WO | 1997/042936 A1 | 11/1997 | |
| WO | 2008/040556 A1 | 4/2008 | |
| WO | WO-2008040556 A1 * | 4/2008 | ............. A61K 35/35 |

OTHER PUBLICATIONS

Elyad M. Davidson et al., A Novel Proliposomal Ropivacaine Oil Pharmacokinetic-Pharmacodynamic Studies After Subcutaneous Administration in Pigs, 2016, 1663-1672, 122(5), Anesthesia Analgesia.
Jean G. Boogaerts et al., Plasma concentrations of bupivacaine after brachial plexus administration of liposome-associated and plain solutions to rabbits, 1993, 1201-1204, 40(12), Can J Anaesth.
Esther M. Pogatzki et al., A mouse model of incisional pain, 2003, 1023-7, 99(4), Anesthesiology.
S R Chaplan et al., Quantitative assessment of tactile allodynia in the rat paw, 1994, 55-63, 53(1), J Neurosci Methods.
Edith Bülbring et al., Biological Comparison of Local Anaesthetics, 1945, 78-84, 85, J Pharmacol Exp Ther.

* cited by examiner

*Primary Examiner* — Svetlana M Ivanova
(74) *Attorney, Agent, or Firm* — Finnegan, Henderson, Farabow, Garrett & Dunner, LLP (57) ABSTRACT

Provided is an anesthetic composition for locally administrating an amide-type anesthetic into a subject in need thereof. The anesthetic composition has multilamellar vesicles with entrapped amide-type anesthetic prepared by hydrating a highly entrapped lipid structure comprising an amide-type anesthetic and a lipid mixture with an aqueous buffer solution at a pH higher than 5.5. Also provided is a method to prepare an anesthetic composition using a simpler and more feasible process for large-scale manufacture and for providing a high molar ratio of amide-type anesthetic to phospholipid content as compared to the prior art. This anesthetic composition has a prolonged duration of efficacy adapted to drug delivery.

16 Claims, 5 Drawing Sheets

SUSTAINED-RELEASE ANESTHETIC COMPOSITIONS AND METHODS OF PREPARATION THEREOF

CROSS-REFERENCE TO RELATED APPLICATIONS

This application is a national stage filing under 35 U.S.C. § 371 of International Application No. PCT/US2018/048329, filed Aug. 28, 2018, which claims the benefit of priority to U.S. Provisional Application No. 62/550,983, filed Aug. 28, 2017, and U.S. Provisional Application No. 62/621,730, filed Jan. 25, 2018, each of which is incorporated by reference in its entirety.

BACKGROUND

Technical Field

The present invention relates to a drug delivery system for delivery of a sustained-release anesthetic composition. The present invention relates to a method of preparing the drug delivery system. The present invention also relates to a sustained-release pharmaceutical composition adapted to a drug delivery system, which has a prolonged duration of efficacy.

Description of Related Art

Several approaches for developing sustained-released local anesthetics have been reported, including 1) preparing multilamellar liposomal local anesthetics using a dehydration-rehydration method (U.S. Pat. No. 6,926,905), 2) preparing giant multivesicular (GMV) liposomal local anesthetics using an ammonium sulfate gradient loading procedure (U.S. Pat. No. 7,357,944), and 3) preparing multivesicular liposomal (MVL) local anesthetics using a water-in-oil procedure (U.S. Pat. No. 8,182,835).

To prepare multilamellar liposomal local anesthetics by the dehydration-rehydration method, phospholipid and cholesterol dissolved in tert-butanol are lyophilized and then hydrated to form multilamellar vesicles (MLVs) and the MLVs are homogenized to obtain small unilamellar vesicles (SUVs). A local anesthetic, for example, bupivacaine, is then dissolved in the SUV solution, followed by lyophilization, hydration, and washing with hyperosmotic saline to remove free bupivacaine.

To prepare GMV liposomal local anesthetics, a thin lipid film is obtained by dissolving lipid in a solvent, removing the solvent, and hydrating with an ammonium sulfate solution to form the MLVs. MLVs are then homogenized to obtain SUVs, which are freeze-thawed to produce GMVs. The external liposomal medium is replaced to create a gradient, an anesthetic—for example, bupivacaine—is actively loaded into the GMVs, and unencapsulated bupivacaine is removed.

To prepare MVL local anesthetics, bupivacaine, for example, is converted to a suitable salt form so that it may be readily dissolved in an aqueous solution, and then the aqueous bupivacaine solution is mixed with a lipid component in an organic solvent with mechanical turbulence to form a water-in-oil emulsion. The water-in-oil emulsion is then dispersed into a second aqueous phase to form solvent spherules. Finally, a MVL local anesthetic is obtained after removing the organic solvent.

In 1991, Legros et al. (U.S. Pat. No. 5,244,678) disclosed preparing MLV liposomal bupivacaine comprising L-α-phosphatidylcholine (EPC) and cholesterol in a molar ratio of 4:3. Afterward, this group disclosed the preparation of liposomal anesthetics by making a lipid film comprised of EPC and an apolar anesthetic, followed by hydrating the lipid film with a pH-controlled buffer in which the apolar anesthetic remains in an uncharged form (U.S. Pat. No. 6,149,937). For example, in preparing liposomal bupivacaine, the lipid film is preferably hydrated with a pH 8.1 buffer (the pKa of bupivacaine is 8.1), which maintains 50% of the bupivacaine in an uncharged form. Legros et al. also disclosed a process for preparing freeze-dried liposome-encapsulated amphiphilic drug compositions (WO1997042936), which are obtained by producing a thin film comprising lipid components and an amphiphilic drug composition, particularly bupivacaine, hydrating the thin film with a pH 8.1 buffer solution to form liposome-encapsulated bupivacaine, freeze drying the liposome-encapsulated bupivacaine together with sorbitol as a membrane stabilizer, and then rehydrating before use to obtain MLV liposomal bupivacaine.

Some of the above-mentioned examples of prior art fail to achieve high entrapment of a drug, i.e., a high drug-to-lipid ratio. Even though some of the examples of prior art illustrate a formulation with a putative high drug-to-lipid ratio, manufacturing these formulations involves tedious procedures and high production costs. There is therefore an unmet need for improved and simplified manufacturing processes for making sustained-release liposomal local anesthetics.

SUMMARY

The present invention provides a method of preparing a sustained-release anesthetic composition using one-step lyophilization to obtain a highly entrapped lipid structure (HELS) comprising a local anesthetic and a lipid mixture including one or more phospholipids and/or cholesterol, and then hydrating the HELS with a pH-controlled buffer solution to form the multilamellar vesicles (MLV) with entrapped local anesthetic and optionally untrapped local anesthetic. This sustained-release anesthetic composition provides a rapid onset of anesthesia and a prolonged duration of local anesthesia with minimal toxicity. In some embodiments, the local anesthetic is an amide-type anesthetic.

An exemplary local anesthetic according to the present invention is an amide-type anesthetic, such as ropivacaine. Other local anesthetics that may be used include lidocaine, bupivacaine, and levobupivacaine. In some embodiments, the HELS according to the present invention is prepared by dissolving apolar ropivacaine, phospholipid, and cholesterol in a solvent system, e.g., tert-butanol alone or a tert-butanol/water cosolvent, followed by removing the solvent system using a lyophilization technique. In some embodiments, a ropivacaine composition is formed by hydrating the HELS with a pharmaceutically acceptable buffer solution at a pH higher than 5.5. The theoretically uncharged ropivacaine is 0.8% of available ropivacaine at pH 6.0 based on the calculation from pKa (the pKa of ropivacaine is 8.1). However, when a pH 6.0 buffer is selected as a hydration solution, the association efficiency (AE) of the resulting anesthetic composition is greater than 64%, which demonstrates that the percentage of uncharged amide-type anesthetic does not make a critical contribution to AE.

The pH value of a pharmaceutically acceptable buffer solution can nevertheless be selected to adjust the ratio of entrapped anesthetic to untrapped anesthetic in the MLVs of an anesthetic composition. In certain embodiments, the molar ratio of amide-type anesthetic to phospholipid ($mol_{drug}$:$mol_{phospholipid}$) in the MLV with entrapped amide-type anesthetic of the anesthetic composition is at least 0.5:1, and can provide a sufficient amount of the amide-type anesthetic to a subject in need thereof to prolong the duration of anesthesia after in viva local administration. In addition, limiting the amount of untrapped amide-type anesthetic can achieve rapid onset anesthesia with minimized maximum plasma concentration ($C_{max}$) exposure.

Other objectives, advantages and novel features of the invention will become more apparent from the following detailed description when taken in conjunction with the accompanying drawings.

BRIEF DESCRIPTION OF THE DRAWINGS

FIGS. 2A and 2B are a series of graphs depicting the effect after SC administration of a ropivacaine composition (circle), ropivacaine (square) and vehicle (triangle) on mouse paw withdrawal thresholds to mechanical stimuli (all data are shown as mean±standard error of the mean (SEM)); FIGS. 3A and 3B are a series of graphs depicting the anesthetic effect over time after single intracutaneous (IC) injection of a ropivacaine composition compared with the same dosage of ropivacaine (all data are shown as mean±SEM)

DETAILED DESCRIPTION OF THE PREFERRED EMBODIMENTS

As employed above and throughout the disclosure, the following terms, unless otherwise indicated, shall be understood to have the following meanings.

As used herein, the singular forms "a", "an," and "the" include the plural reference unless the context clearly indicates otherwise.

All numbers herein may be understood as modified by "about," which, when referring to a measurable value such as an amount, a temporal duration, and the like, is meant to encompass variations of ±10%, preferably ±5%, more preferably ±1%, and even more preferably ±0.1% from the specified value, as such variations are appropriate to obtain a desired amount of drug, unless other specified.

"Association efficiency" (AE) represents the amount of drug substance entrapped by multilamellar vesicles (MLVs) in an anesthetic composition and is calculated by the ratio of the drug substance amount entrapped in MLVs to the drug substance amount in the original anesthetic composition. MLV with entrapped drug can be obtained by known methods in the art according to the physical properties of the MLV and the general knowledge in the field of the art. Preferably, MLV with entrapped drug substance can be obtained by separating the untrapped drug from an anesthetic composition using centrifugation methods, e.g., traditional centrifugation, density gradient centrifugation, differential centrifugation, or by filtration methods, e.g., diafiltration, gel filtration, membrane filtration.

Multilamellar Vesicle

The term "multilamellar vesicle (MLV)" or "multilamellar vesicles (MLVs)" as used herein refers to a particle characterized by having an aqueous interior space sequestered from an outer medium by a membrane of one or more bilayers forming a vesicle. Bilayer membranes of multilamellar vesicles are typically formed by lipids, i.e., amphiphilic molecules of synthetic or natural origin that comprise spatially separated hydrophobic and hydrophilic domains. In certain embodiments of the present invention, a multilamellar vesicle forms by more than one layer of lipid bilayer membrane.

In general, bilayer membranes of MLV comprise a lipid mixture typically including dialiphatic chain lipids, such as phospholipids, diglycerides, dialiphatic glycolipids, single lipids such as sphingomyelin and glycosphingolipid, steroids such as cholesterol and derivates thereof, and combinations thereof. Examples of phospholipids according to the present invention include, but are not limited to, 12-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-seine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-9n-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE).

Local Anesthetics

The term "local anesthetics" refers to one or more groups of substances causing loss of sensation in a circumscribed area of a subject caused by depression of excitation in nerve endings or inhibition of the conduction process in peripheral nerves. In some embodiments, the local anesthetics are amide-type anesthetics. The typical amide-type anesthetic structure contains a lipophilic part and a hydrophilic part that connect by an —NHCO— linkage near the center of the molecule. Suitable amide-type anesthetics include, but are not limited to, lidocaine, bupivacaine, levobupivacaine, ropivacaine, mepivacaine, pyrrocaine, articaine, and prilocaine. In certain embodiments, the amide-type anesthetic is ropivacaine base.

Highly Entrapped Lipid Structure

The term "highly entrapped lipid structure" (HELS) refers to a solid phase lyophilized cake or dried powder containing a lipid mixture and one or more amide-type anesthetics, which can be manufactured, stored long-term so as to extend the shelf life of the composition, and hydrated immediately prior to clinical use. The lipid mixture described above can comprise one or more phospholipids without cholesterol or can comprise one or more phospholipids with a mole percentage of cholesterol of no more than 50% relative to the amount of the total lipid mixture. Alternatively, the mole percentage of cholesterol on the basis of the lipid mixture is from about 0% to about 50%, and optionally from about 33% to about 40%. In some embodiments of the present invention, the phospholipid(s) and cholesterol are at a molar ratio of from 1:1 to 3:1.

The HELS can be prepared by 1) dissolving a lipid mixture and one or more amide-type anesthetics in a solvent system to form a liquid structure comprising one or more solvents to form a homogeneous solution, and 2) removing the solvent(s) to solidify the formulation of the lipid mixture and the amide-type anesthetic(s). Solvent removal can be performed using known techniques such as freeze drying (lyophilization) or spray drying. Examples of solvent systems suitable for freeze drying include, but are not limited to, tert-butanol and tert-butanol/water cosolvent systems with or without other non-aqueous solvents such as acetone, acetonitrile, ethanol, n-propanol, isopropanol, n-butanol, methanol, dichloromethane, dimethyl sulfoxide, and carbon tetrachloride. Examples of solvent systems suitable for spray drying include, but are not limited to, water, ethanol, methanol, chloroform, dichloromethane, diethyl ether, carbon tetrachloride, ethyl acetate, and dioxane.

Anesthetic Composition

The term "anesthetic composition" refers to a multilamellar vesicle (MLV) product suitable for local administration. In certain embodiments, an anesthetic composition comprises an amide-type anesthetic entrapped by MLVs as well as untrapped amide-type anesthetic. The term "entrap" or "entrapment" refers to bilayer membrane of MLVs encapsulating, embedding, or associating with a target drug substance. The MLVs with entrapped amide-type anesthetic can be obtained by known methods in the art, preferably, by separating the untrapped amide-type anesthetic from anesthetic composition using centrifugation methods, e.g., traditional centrifugation, density gradient centrifugation, differential centrifugation, or by filtration methods, e.g., diafiltration, gel filtration, membrane filtration. The size distribution of the MLVs with entrapped amide-type anesthetic according to the present invention can be determined by various known methods in the art. An exemplary particle size of MLVs with entrapped amide-type anesthetic is no less than 1 µm; and optionally, is more than 5 µm, such as at a range from 5 µm to 50 µm, or from 10 µm to 25 µm. Alternatively, the median diameter (D50) of the MLVs with entrapped amide-type anesthetic of the anesthetic composition is no less than 1 µm; and, optionally, is more than 5 µm, such as at a range from 5 µm to 50 µm, or from 10 µm to 25 µm.

To prepare the anesthetic composition for use, the HELS is hydrated with an aqueous buffer solution at a pH value higher than 5.5. In some embodiments, the aqueous buffer solution is at a pH range of from 5.5 to 8.0, and optionally of from 6.0 to 7.5.

Suitable aqueous buffer solutions according to the present invention include, but are not limited to, citrate, acetate, malate, piperazine, succinate, 2-(N-morpholino)ethanesulfonic acid (MES), histidine, bis-tris, phosphate, ethanolamine, N-(2-acetamido)iminodiacetic acid (ADA), carbonate, N-(2-acetamido)-2-aminoethanesulfonic acid (ACES), 1,4-piperazinediethanesulfonic acid (PIPES), 3-morpholino-2-hydroxypropanesulfonic acid (MOPSO), imidazole, N,N-bis(2-hydroxyethyl)-2-aminoethanesulfonic acid (BES), 4-(2-hydroxyethyl)piperazine-1-ethanesulfonic acid (HEPES), triethanolamine, lysine, tris, and glycylglycine. The amount of untrapped amide-type anesthetic in the composition can be adjusted based on the distribution-coefficient of the anesthetic by selecting an appropriate pH value for the aqueous buffer solution based on the clinical indication and the total injection dosage.

In some embodiments, the aqueous buffer solution comprises histidine at a concentration ranging from 1 mM to 200 mM, from 10 mM to 150 mM, or from 40 mM to 120 mM.

The amount of untrapped amide-type anesthetic is a function of the association efficiency (AE) of the anesthetic composition, which is determined by a centrifugation method. Mathematically, the amount of untrapped amide-type anesthetic is expressed as follows:

$$A_{untrapped} = A_{total} \times (1-AE)$$

wherein $A_{untrapped}$ is the amount of untrapped amide-type anesthetic; $A_{total}$ is the total amount of amide-type anesthetic in the anesthetic composition; and AE is obtained by dividing the amount of amide-type anesthetic entrapped in MLVs by the total amount of amide-type anesthetic in the anesthetic composition. AE according to the present invention is at least 60%, and, optionally, from 70% to 95%.

The molar ratio of amide-type anesthetic to phospholipid ($mol_{drug}:mol_{phospholipid}$, D:PL) of the MLVs with entrapped amide-type anesthetic is preferably at least 0.5:1, including but not limited to 0.7:1, 0.9:1, 1.2:1, or 1.4:1, and the median diameter (D50) of the MLVs with entrapped amide-type anesthetic is preferably not less than 1 µm, for example, not less than 5 µm; and, optionally, within a range from 5 µm to 20 µm, or from 5 µm to 15 µm.

The amide-type anesthetic concentration of the anesthetic composition should be higher than 2 mg/mL to achieve a clinical therapeutic benefit. Suitable amide-type anesthetic concentrations include but are not limited to from 2 mg/mL to 30 mg/mL and from 10 mg/mL to 20 mg/mL. The restricted amount of untrapped anesthetic in the anesthetic compositions of the invention can provide the benefit of achieving a higher maximum tolerance dosage (depending on the plasma anesthetic concentration that causes central nervous system and cardiovascular system toxicity) and can be used to provide rapid-onset efficacy. In some embodiments, the $C_{max}$ after administration of a ropivacaine composition is 16.7% of that after administration of unformulated ropivacaine, which indicates that a 6-fold higher approved clinical dosage may be used within the safety window of this anesthetic.

For clinical use, AE in certain embodiments of the invention ranges from 70% to 95%. The remaining MLVs with entrapped amide-type anesthetic act as a depot to release the amide-type anesthetic into the local environment gradually in a manner that maintains the therapeutically effective dosage at the local site. In some embodiments, the half-life of ropivacaine derived from a single SC administration of a ropivacaine composition according to the invention is prolonged at least 10-fold compared to that of unformulated ropivacaine. The duration of the anesthetic effect after administration of the ropivacaine composition of the invention significantly extends beyond that of unformulated ropivacaine.

The disclosure will be further described with reference to the following specific, non-limiting examples.

EXAMPLES

The following examples illustrate the preparation and properties of certain embodiments of the present invention.

Example 1

Preparation of Ropivacaine Compositions

HSPC and DMPC were purchased from NOF Corporation. Cholesterol was purchased from Sigma-Aldrich and ropivacaine was purchased from Apollo Scientific or Dishman. All other chemicals were purchased from Sigma-Aldrich.

To prepare several HELSs, different lipid mixtures with ropivacaine at the following molar ratios: HSPC:cholesterol:ropivacaine=1.5:1:2.2, HSPC:cholesterol:ropivacaine=2:1:2.9, DMPC:cholesterol:ropivacaine=2:1:2.9, and DMPC:DPPG:cholesterol:ropivacaine=1.85:0.15:1:2.9 were used. The lipids and ropivacaine were mixed and then dissolved in tert-butanol or a tert-butanol/water cosolvent system (1/1, vol/vol) to form the liquid structures. Each liquid structure sample was frozen for 30 to 60 minutes and then was lyophilized overnight to obtain HELS in a lyophilized cake form.

To prepare the lipid structures for the vehicle control, a lipid mixture with a molar ratio of DMPC:cholesterol=2:1 was weighed and then dissolved in ten-butanol. The resulting sample was frozen for 60 minutes and then was lyophilized overnight to obtain a lyophilized cake of vehicle.

The lyophilized cakes were hydrated with different buffers at different pH values at suitable temperatures (for instance, higher than 25° C./ambient temperature (AT) for DMPC and higher than 60° C. for HSPC) for 2 to 10 minutes to form ropivacaine compositions and vehicle compositions, respectively.

Example 2

Characterization of Ropivacaine Compositions

The association efficiency (AE) of each above-described preparation was determined as follows. Two hundred microliters of each ropivacaine composition were transferred to a centrifuge and spun for 5 min at 3000×g at 4° C. After decanting the supernatant, MLVs with entrapped ropivacaine were obtained and re-suspended to a final volume of 200 μL. A reference absorbance standard was established for each drug substance (e.g., ropivacaine) based on solutions of the test drug substance of known concentration. The drug amounts of both the original ropivacaine composition and the MLVs with entrapped ropivacaine were measured using an ultraviolet/visible (UV/Vis) spectrophotometer. The AE represents the ratio of the drug amount in the MLVs with entrapped ropivacaine to the drug amount in the ropivacaine composition. The D:PL of MLVs with entrapped ropivacaine was calculated by multiplying the D:PL of the HELS by AE. A summary of the results is shown in Table 1.

The particle size of each ropivacaine composition was measured using a laser diffraction analyzer (LA-950V2, Horiba). The median diameter (D50) of the MLVs with entrapped ropivacaine formed by hydrating the HELS (DMPC:cholesterol=2:1) with 50 mM histidine buffer (pH 6.5) was 11.1±0.3 μm (n=3).

TABLE 1

The AE and calculated molar ratio of amide-type anesthetic to phospholipid (D:PL) from various formulations

| Lipid composition | Hydration condition | | | Ropivacaine concentration (mg/mL) of ropivacaine composition | AE (%) | Calculated D:PL ratio of MLVs with entrapped ropivacaine |
|---|---|---|---|---|---|---|
| | Buffers | pH | Temp | | | |
| HSPC:cholesterol = 3:2 | 100 mM citrate buffer in 0.9% NaCl solution | 5.0 | 60 | 17.6 | 22 | 0.32 |
| HSPC:cholesterol = 3:2 | 100 mM histidine buffer in 0.9% NaCl solution | 6.0 | 60 | 17.1 | 64 | 0.93 |
| HSPC:cholesterol = 3:2 | 50 mM phosphate buffer | 6.5 | 60 | 16.9 | 89 | 1.30 |
| HSPC:cholesterol = 3:2 | 50 mM histidine buffer | 6.5 | 60 | 17.9 | 93 | 1.36 |
| HSPC:cholesterol = 3:2 | 100 mM histidine buffer in 0.9% NaCl solution | 7.0 | 60 | 18.3 | 86 | 1.25 |
| HSPC:cholesterol = 3:2 | 100 mM tris buffer in 0.9% NaCl solution | 8.0 | 60 | 17.7 | 100 | 1.46 |
| HSPC:cholesterol = 2:1 | 50 mM histidine buffer | 6.0 | 60 | 19.2 | 94 | 1.37 |
| DMPC:cholesterol = 2:1 | 50 mM histidine buffer | 5.5 | AT | 18.6 | 71 | 1.03 |
| DMPC:cholesterol = 2:1 | 50 mM histidine buffer | 6.0 | AT | 17.8 | 84 | 1.22 |
| DMPC:cholesterol = 2:1 (cosolvent) | 50 mM histidine buffer | 6.0 | AT | 17.1 | 82 | 1.20 |
| DMPC:cholesterol = 2:1 | 50 mM histidine buffer | 6.5 | AT | 17.5 | 90 | 1.31 |

Example 3

Pharmacokinetic Study of Ropivacaine Compositions

Jugular vein cannulated (JVC) female Sprague-Dawley rats were used for a pharmacokinetic (PK) study. The rats were housed in a holding room that operates on a 12-hr light/12-hr dark circadian cycle and that provides free access to water and food. The ropivacaine compositions were prepared according to Example 1, wherein HELSs of DMPC:cholesterol:ropivacaine=2:1:2.9 were hydrated with 50 mM histidine buffers at pH 5.5, 6.0, and 6.5, respectively. Unformulated ropivacaine was prepared by dissolving ropivacaine hydrochloride monohydrate in 0.9% NaCl to 24.0 mg/mL. The in vim, PK profiles of the respective liposomal ropivacaine compositions and of unformulated ropivacaine administered to groups of rats (n=3 or 4 per group) were compared following subcutaneous (SC) injection at a dosage of 20.0 mg/kg of ropivacaine. Blood samples were collected at 15 min, 1 hour, 2 hours, 4 hours, 8 hours, 24 hours, 48 hours, and 72 hours post-injection. Plasma samples were obtained by centrifugation and were kept frozen at –80® C. until analysis. PK data obtained from the samples were analyzed using a noncompartmental model (WinNonlin® software). The PK parameters derived from this model are shown in Table 2.

TABLE 2

PK parameters derived from rats after single SC administration of ropivacaine compositions or unformulated ropivacaine

| Parameter | Ropivacaine | Ropivacaine composition | | |
| --- | --- | --- | --- | --- |
| | | Hydrated with pH 5.5 histidine solution | Hydrated with pH 6.0 histidine solution | Hydrated with pH 6.5 histidine solution |
| n | 4 | 3 | 4 | 4 |
| $T_{1/2}$ (h) | 3.1 ± 1.4 | 33.9 ± 24.3 | 31.8 ± 16.9 | 34.9 ± 16.0 |
| $C_{max}$ (ng/mL) | 801.8 ± 208.0 | 444.7 ± 74.0 | 284.5 ± 61.3 | 133.5 ± 34.8 |
| $T_{max}$ (h) | 1.8 ± 0.5 | 1.7 ± 0.6 | 1.5 ± 0.6 | 1.5 ± 0.6 |
| $AUC_{0-t}$ (h × ng/mL) | 4035 ± 632 | 3415 ± 142 | 3511 ± 462 | 3665 ± 930 |

Figure 1:
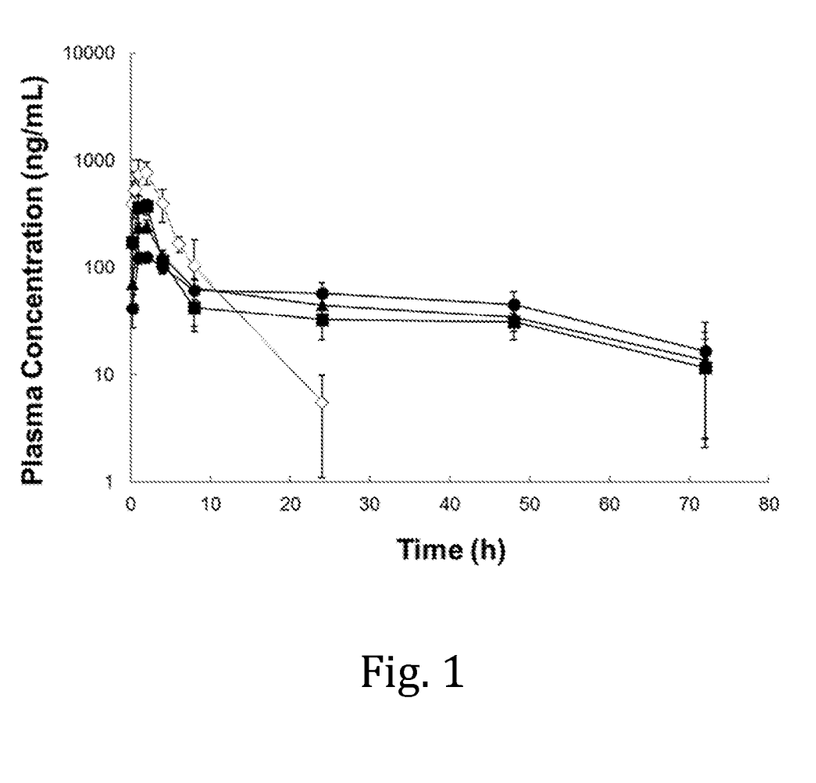
FIG. 1 is a graph showing the plasma concentration of ropivacaine in rats after subcutaneous (SC) injection of a ropivacaine composition (hydrated with a pH 5.5 histidine solution, closed square; hydrated with a pH 6.0 histidine solution, closed triangle; and hydrated with a pH 6.5 histidine solution, closed circle) or after SC injection of unformulated ropivacaine (open diamond) (all data are shown as mean±standard deviation (SD))

The $C_{max}$ of ropivacaine composition was lower when the pH value of the hydration solution was more alkaline. Compared to the unformulated ropivacaine group, the $C_{max}$ was 55.5% for ropivacaine composition hydrated with the pH 5.5 histidine solution, 35.5% for ropivacaine composition hydrated with the pH 6.0 histidine solution, and 16.7% for ropivacaine composition hydrated with the pH 6.5 histidine solution. The half-life ($T_{1/2}$) of all three ropivacaine compositions was significantly prolonged compared with that of unformulated ropivacaine. Based on the area under the curve ($AUC_{0-4}$), 84.6% to 90.8% of the ropivacaine was released 72 hours after injection of the ropivacaine composition. The results of the PK study are shown in FIG. 1. After administration of the same dosage, ropivacaine in the plasma could be detected until 72 hours in all ropivacaine composition groups, however, ropivacaine could not be detected in the plasma after 24 hours in the unformulated ropivacaine group.

Example 4

Anesthetic Effect in a Paw Incision Mouse Model

Wild type male C57/BL6 mice (8-week-old, Envigo) were used for evaluating the anesthetic efficacy after paw incision as described in Anesthesiology, 2003 October; 99(4): 1023-7 and J Neurosci Methods, 1994 July; 53(1): 55-63. The mouse holding room operates on a 12-hour light/12-hour dark circadian cycle to ensure lights are not used and that researchers and technicians do not enter the mouse room during the dark cycle. The ropivacaine composition and vehicle were prepared according to Example 1, wherein a HELS of DMPC:cholesterol:ropivacaine=2:1:2.9 and a vehicle's lipid structure of DMPC:cholesteol=2:1 were each hydrated with 50 mM histidine buffer at pH 6.0. Unformulated ropivacaine was prepared by dissolving ropivacaine in a 9.4% sucrose solution containing 0.1 N HCl at 18.3 mg/mL. The in vivo efficacy study of the ropivacaine composition, unformulated ropivacaine, and vehicle (n=8 per group) were compared following SC injection after paw incision at the dosage of 0.18 mg ropivacaine per incision.

Baseline (T=–2 hours) mechanical (von Frey) thresholds of 32 mice were taken prior to surgery; baseline thresholds were measured on the mouse's left hind paw. All 32 mice received a plantar incision (5 mm long and 5 mm depth) on their left hind paw. Two-hours post-surgery (T=0 hour), the mechanical threshold of each mouse was reassessed and the presence of mechanical allodynia in each mouse was confirmed. Thirty-two mice were randomized into 4 groups (8 mice per group). While anesthetized with 2.5% isoflurane anesthesia, each mouse received a SC injection of vehicle (10 µL), ropivacaine composition (10 µL of 18.3 mg/mL) or unformulated ropivacaine (10 µL of 18.3 mg/mL). The 50% paw withdrawal threshold of each mouse was obtained using the up-down method at baseline time point (–2), and the designated time points (0, 1, 2, 3, 4, 5, 6, 8, and 24 hours) after SC injection treatment.

Figure 2A:
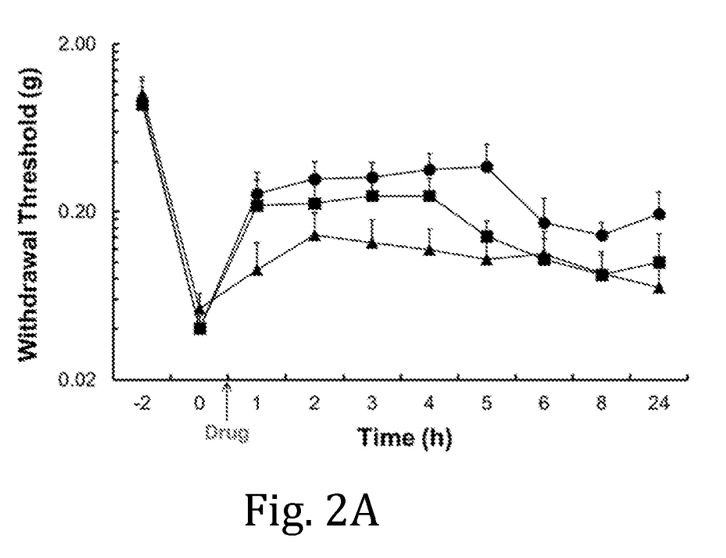
FIG. 2A is a graphical plot of time versus the withdrawal threshold (g)
Figure 2B:
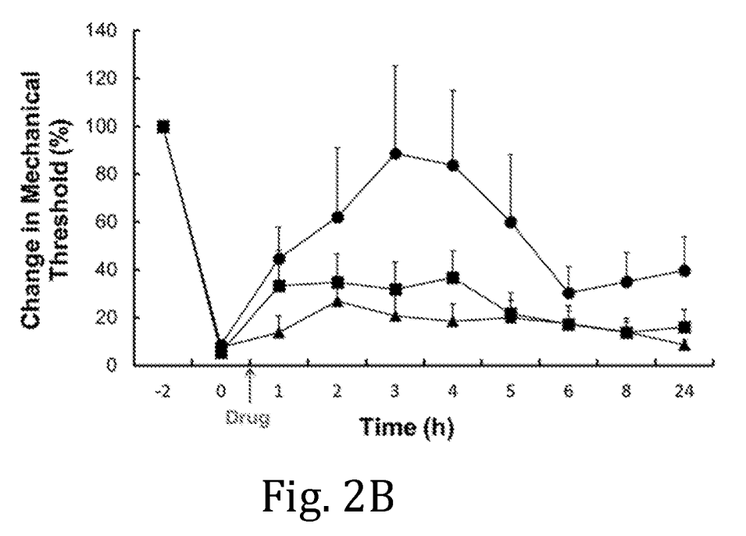
FIG. 2B is a graphical plot of time versus the change in mechanical threshold (%)

The anesthetic efficacy of the ropivacaine composition (circle), unformulated ropivacaine (square) and vehicle (triangle) after paw incision is shown in FIGS. 2A and 2B. The average 50% withdrawal threshold for each treatment group was graphed; data presented as a withdrawal threshold (g) were plotted against time (FIG. 2A). To account for variability among the baseline mechanical sensitivities of individual mice, each mouse's 50% paw withdrawal thresholds after surgery and treatment were normalized to its own baseline 50% withdrawal threshold (T=–2 hours). The average normalized 50% withdrawal threshold for each treatment group was graphed; data presented as a % change in mechanical threshold relative to baseline thresholds were plotted against time (FIG. 2B). The onset time of ropivacaine composition and unformulated ropivacaine anesthesia after administration was similar, with the withdrawal threshold increased from 0.04 g to 0.26 g and 0.22 g, respectively, at the first time point (T=1 hour). The ropivacaine composition group produced the largest (~88%) and longest (at least 5 hours) analgesic action, and the unformulated ropivacaine group also produced some degree of analgesia compared to vehicle group.

Example 5

Anesthesia Effect on Guinea Pigs Using a Modified IC Wheat Pin-Prick Model

Male guinea pigs (8-weeks-old, around 500 g, Charles River Laboratories) were employed to evaluate the anesthetic efficacy as described in J Pharmacol Exp Ther. 1945; 85: 78-84. All guinea pigs were housed in group cages with 2 animals per cage, with Guinea Pig food (Healthy Pet®) and water ad libitum in order to ensure proper nurturing and enrichment. The housing condition was controlled at 65-75° F. (~8-23° C.) with a 12-hour light/12-hour dark circadian cycle. After an initial period of acclimatization to laboratory conditions for 12 days, the guinea pigs were randomly designated as No. 1 to No. 8. The ropivacaine composition was prepared according to Example 1, wherein a HELS of DMPC:cholesterol:ropivacaine, 2:1:2.9 was hydrated with 50 mM histidine buffer at pH 6.0. Unformulated ropivacaine was prepared by dissolving ropivacaine hydrochloride monohydrate in ultrapure water to 20.5 mg/mL.

This in vivo efficacy study of the guinea pigs (n=4 or 6 per group) compared the ropivacaine composition and unformulated ropivacaine following intracutaneous (IC) injection at a dosage of 3.0 mg of ropivacaine per IC wheal and 1.5 mg of ropivacaine per IC wheal, respectively. The backs of the guinea pigs were shaved one day before the experiment. On the experimental day, four areas were drawn on the back before the drug administration and the sensitivity of these areas was determined by a pin-prick. Each animal received four designated formulations on the back, which created 4 wheals, respectively. The reaction to pin-pricks at the injection site was tested at 0 min, 15 min, 1 hour, 2 hours, 4 hours, 5 hours, 6 hours, 8 hours, 10 hours, 12 hours, and 23 hours following injection of the formulation. The pin-pricks were applied first to a control area outside the wheal at each time point. After observing the animal's normal reaction to the pin-prick outside the wheal, six pricks were applied inside the wheal and the pricks to which the guinea pig failed to react were recorded as non-responses. Animals that displayed a 100% response for all pricks were not monitored at further time points.

Figure 3A:
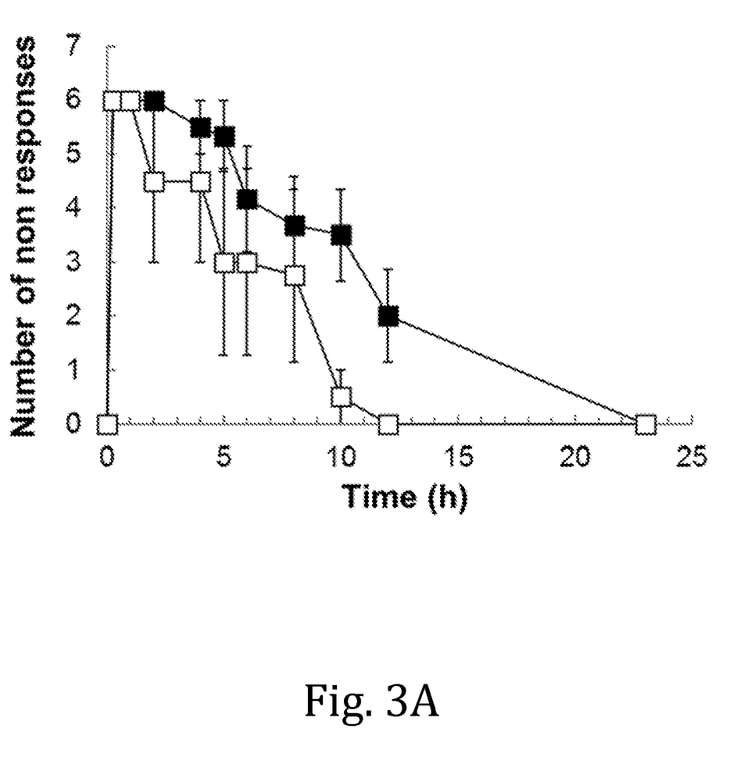
FIG. 3A illustrates the anesthetic effect on the guinea pig cohort dosed at 3.0 mg per IC wheal of ropivacaine composition (closed square) or ropivacaine (open square)
Figure 3B:
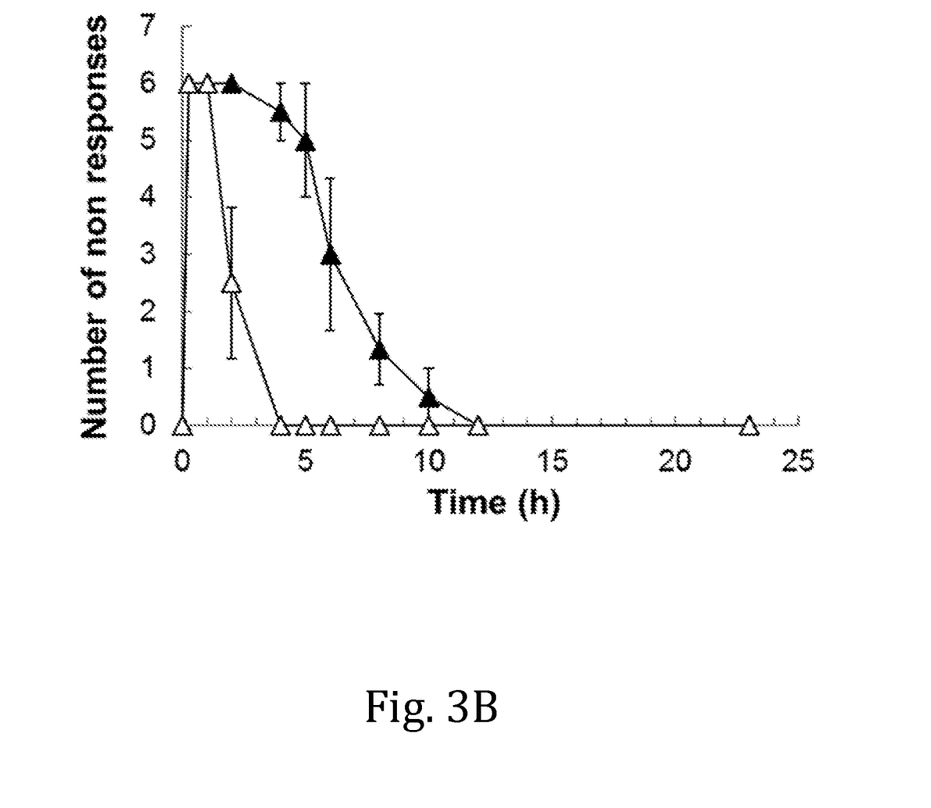
FIG. 3B illustrates the anesthetic effect on the guinea pig cohort dosed at 1.5 mg per IC wheal of ropivacaine composition (closed triangle) or ropivacaine (open triangle).

The anesthetic effects of the ropivacaine composition group compared with the unformulated ropivacaine group at the same dosage were determined and the results are depicted in FIGS. 3A and 3B. Onset of anesthesia for both the ropivacaine composition and unformulated ropivacaine at both the 3.0 mg (FIG. 3A) and 1.5 mg ropivacaine (FIG. 3B) dosages was observed at the first time point, within 15 min. The ropivacaine composition group exhibited sustained anesthetic effects compared to what was observed for the unformulated ropivacaine group for both dosages. For a dosage of 3 mg of ropivacaine per IC wheal, a significantly sustained anesthetic effect was observed at 10 hours and 12 hours post injection ($p<0.05$) for the ropivacaine composition group compared to the unformulated ropivacaine group. For a dosage of 1.5 mg of ropivacaine per IC wheal, the anesthetic effect was also sustained longer for the ropivacaine composition group compared to the unformulated ropivacaine group, and significant differences ($p<0.05$) were observed at 2 hours, 4 hours, and 5 hours post-injection.

What is claimed is:

1. A method of preparing a sustained-release anesthetic composition, comprising:
    creating a highly entrapped lipid structure (HELS) comprising:
        at least one amide-type local anesthetic in a free base form, and
        a lipid mixture including at least one phospholipid, and
    hydrating the HELS with an aqueous buffer solution at a pH of 5.5 to 8.0 to obtain the sustained-release anesthetic composition for locally administering the amide-type local anesthetic to a subject in need thereof; wherein hydrating the HELS forms multilamellar vesicles (MLVs) that entrap the amide-type local anesthetic; the median diameter of the MLVs with the entrapped amide-type local anesthetic is at least 1 µm; and the molar ratio of the entrapped amide-type local anesthetic to phospholipid in the MLVs is at least 0.5:1.

2. The method according to claim 1, wherein the HELS is in a form of a cake, powder, non-film solid bulk, or a combination thereof.

3. The method according to claim 1, wherein the method of creating the HELS comprises:
    dissolving the lipid mixture and the at least one amide-type local anesthetic in a solvent system to form a liquid structure; and
    removing the solvent system from the liquid structure.

4. The method according to claim 3, wherein the step of removing the solvent system includes lyophilizing or spray drying the liquid structure.

5. The method according to claim 3, wherein the solvent system includes tert-butanol or a tert-butanol/water cosolvent.

6. The method according to claim 1, wherein the lipid mixture comprises cholesterol.

7. The method according to claim 6, wherein the mole percentage of cholesterol in the lipid mixture is not more than 50%.

8. The method according to claim 6, wherein the at least one phospholipid and cholesterol are at a molar ratio of from 1:0.01 to 1:1.

9. The method according to any of claims 1 to 8, wherein the at least one amide-type local anesthetic is lidocaine, bupivacaine, levobupivacaine, ropivacaine, mepivacaine, pyrrocaine, articaine, or prilocaine.

10. The method according to any of claims 1 to 8 wherein the at least one amide-type local anesthetic is ropivacaine base.

11. The method according to any of claims 1 to 8, wherein the aqueous buffer solution comprises histidine at a concentration ranging from 1 mM to 200 mM.

12. A sustained-release anesthetic composition for locally administering at least one amide-type local anesthetic in a free base form to a subject in need thereof, wherein the composition is prepared by the method according to any of claims 1 to 8; the median diameter of the MLVs that entrap the amide-type local anesthetic is at least 1 µm; and the molar ratio of the amide-type local anesthetic to phospholipid in the MLVs is at least 0.5:1.

13. The sustained-release anesthetic composition according to claim 12, wherein the at least one amide-type local anesthetic is ropivacaine base.

14. The sustained-release anesthetic composition according to claim 12, wherein the aqueous buffer solution comprises histidine at a concentration ranging from 1 mM to 200 mM.

15. The method of according to claim 1, wherein the at least one phospholipid is phosphatidylcholine.

16. The method of according to claim 1, wherein the phosphatidylcholine is hydrogenated soy phosphatidylcholine.

* * * * *